Figure 1:
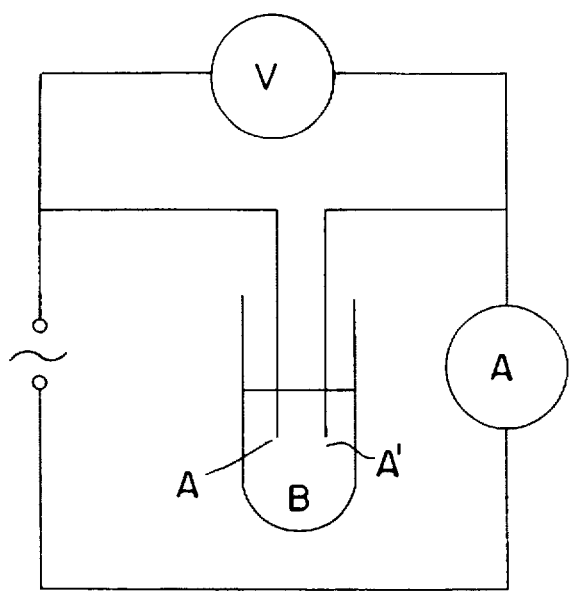

United States Patent [19]

Mayer et al.

[11] Patent Number: 5,789,191
[45] Date of Patent: Aug. 4, 1998

[54] METHOD OF DETECTING AND COUNTING MICROORGANISMS

[75] Inventors: Bianca Mayer, Hamburg; Gerhard Sauermann, Wiemersdorf; Bernd Traupe; Florian Wolf, both of Hamburg, all of Germany

[73] Assignee: Beiersdorf AG, Hamburg, Germany

[21] Appl. No.: 602,748

[22] PCT Filed: Aug. 17, 1994

[86] PCT No.: PCT/DE94/00953

§ 371 Date: Feb. 21, 1996

§ 102(e) Date: Feb. 21, 1996

[87] PCT Pub. No.: WO95/06133

PCT Pub. Date: Mar. 2, 1995

[30] Foreign Application Priority Data

Aug. 26, 1993 [DE] Germany ............... 43 28 689.5

[51] Int. Cl.[6] ............... C12Q 1/06; C12Q 1/04; C12Q 1/18; C12Q 1/02
[52] U.S. Cl. ............... 435/39; 435/34; 435/32; 435/30; 435/29; 435/36; 435/38; 435/255.1; 435/254.22; 435/254.2; 435/848; 435/849; 435/882; 435/883; 435/884; 435/921; 435/922; 435/923
[58] Field of Search ............... 435/39, 34, 32, 435/30, 29, 36, 38, 882, 883, 884, 921, 922, 923, 255.1, 254.22, 254.2, 848, 849

[56] References Cited

U.S. PATENT DOCUMENTS

| 3,743,581 | 7/1973 | Cady et al. ............... 435/817 |
| 3,984,766 | 10/1976 | Thornton ............... 422/50 |
| 4,160,205 | 7/1979 | Hobbs et al. ............... 435/39 |
| 4,288,544 | 9/1981 | Suzuki et al. ............... 435/817 |

(List continued on next page.)

FOREIGN PATENT DOCUMENTS

| 0 036 274 B1 | 9/1981 | European Pat. Off. . |
| 0 397 362 A1 | 11/1990 | European Pat. Off. . |
| 2 322 641 | 11/1974 | Germany . |
| 27 47 033 | 4/1978 | Germany . |

(List continued on next page.)

OTHER PUBLICATIONS

Larson et al. "J. Clinical Microbiology", pp. 604–608, Mar. 1986.

*Primary Examiner*—Louise Leary
*Attorney, Agent, or Firm*—Sprung Kramer Schaefer & Briscoe

[57] ABSTRACT

The invention provides a cosmetic or dermatological method for detecting and/or selectively quantifying individual microorganisms, and/or whole groups of microorganisms, which are present on human or animal skin, comprising the steps of removing a sample of the microflora of the human or animal skin, treating the sample with a deinhibiting medium, adding the treated sample to a culture medium which exhibits favorable growth conditions for a defined group of microorganisms but unfavorable growth conditions for other microorganisms, to produce a selective culture, and incubating the selective culture over a sufficiently long period of time, to allow only the group of microorganisms for which the culture medium exhibits favorable growth conditions the opportunity to multiply, in association with metabolic products, in particular $CO_2$, produced which collect either in the culture medium itself or in a test vessel which is provided for the purpose and which contains an indicator medium, and the concentration of the metabolic products is elucidated by means of the change in the alternating current (AC) resistance of the culture medium and/or the indicator medium in the test vessel and, after appropriate calibration, is correlated by means of arithmetical methods with the number of microorganisms in the selective medium.

17 Claims, 1 Drawing Sheet

U.S. PATENT DOCUMENTS

| | | | |
|---|---|---|---|
| 4,490,235 | 12/1984 | Calzi | 422/50 |
| 4,810,650 | 3/1989 | Kell et al. | 422/50 |
| 5,425,361 | 6/1995 | Fenzlein et al. | 422/50 |
| 5,541,082 | 7/1996 | Botchner | 435/34 |

FOREIGN PATENT DOCUMENTS

| | | |
|---|---|---|
| 32 26 552 A1 | 2/1983 | Germany . |
| 41 39 122 C1 | 4/1993 | Germany . |
| 642 398 | 4/1984 | Switzerland . |
| 1686354 | 10/1991 | U.S.S.R. . |
| 1686354 A1 | 10/1991 | U.S.S.R. . |
| 1 433 887 | 4/1976 | United Kingdom . |
| WO 92/04630 | 3/1992 | WIPO . |
| WO 93/14402 | 7/1993 | WIPO . |

METHOD OF DETECTING AND COUNTING MICROORGANISMS

The present invention relates to a method for qualitatively detecting and quantitatively counting microorganisms, in particular those microorganisms which colonize the human skin. In addition, the present invention relates to agents for use in such methods.

Microorganisms are differentiated into prokaryotic microorganisms, that is those without any actual cell nucleus, and eukaryotic microorganisms, that is those having a cell nucleus.

The eukaryotes include algae, fungi and protozoa. The prokaryotes include bacteria. Bacteria are, in turn, classified into eubacteria, filament-forming bacteria, prosthecate and budding bacteria, actinomycetes, obligately parasitic bacteria, spirochaetes, cyanobacteria, archaebacteria and others.

Eubacteria are essentially subdivided into cocci, that is spherical bacteria (e.g. streptococci), essentially rod-shaped or elongate cylindrical non-sporulating bacteria (e.g. coryneform bacteria, propionibacteria, pseudomonads, enterobacteria, spore-forming rods (e.g. bacilli and clostridia) and curved rods (e.g. spirilla and vibrios).

In addition, the eubacteria can be subdivided, over and above the previously described groups, into Gram-positive and Gram-negative bacteria, that is bacteria whose cell wall is stained blue after the Gram test even after washing with alcohol, or those whose cell wall is washed colourless once again by the alcohol.

As a consequence of the structure of their cell walls, Gram-positive and Gram-negative bacteria possess differing properties; for example penicillin, which intervenes in the process of cell wall formation, principally has a lethal effect on Gram-positive bacteria (although on some Gram-negative bacteria as well).

Microorganisms in general, and bacteria in particular, are practically ubiquitous. For example, mycobacteria, streptococci, staphylococci and propionibacteria, in the main, can be found on healthy human skin. Coryneform bacteria, which are also present on the skin, have recently been identified as being responsible for the production of an unpleasant body odour due to the decomposition of apocrine sweat.

Fungi, also termed mycota |mykes=Greek for fungus| or mycobionts, are included in the eukaryotes. Eukaryotes are living creatures whose cells (eucytes), in contrast to those of the so-called prokaryotes (procytes), possess a cell nucleus which is delimited from the remainder of the cytoplasm by means of a nuclear coat and nuclear membrane. The cell nucleus contains the hereditary information, which is stored in chromosomes.

Representatives of the mycobionts include, for example, yeasts (Protoascomycetes), moulds (Plectomycetes), mildew (Pyrenomycetes), downy mildew (Phycomycetes) and, of course, the upright fungi (Basidiomycetes).

While the fungi, including the Basidiomycetes, are not vegetable organisms, they do, like these, have a cell wall, vacuoles which are filled with cell sap, and a flow of plasm which is readily visible in the microscope. They do not contain any photosynthetic pigments and are C-heterotrophic. They grow under aerobic conditions and obtain energy by oxidizing organic substances. However, some representatives, for example yeasts, are facultative anaerobic organisms and are able to obtain energy by means of fermentation processes.

Dermatomycoses are diseases in which certain fungal species, in particular dermatophytes, penetrate the skin and hair follicles. Examples of the symptoms of dermatomycoses are blisters, exfoliation, rhagades and erosion, usually associated with itching or allergic eczema.

Dermatomycoses can essentially be subdivided into the following four groups: dermatophytoses (e.g. epidermophytosis, favus, microsporosis and trichophytosis), yeast mycoses (e.g. pityriasis, Candida infections, blastomycosis, Busse-Buschke disease, torulosis, piedra alba, torulopsidosis and trichosporosis), mould mycoses (e.g. aspergillosis, cephalosporidosis, phycomycosis and scopulariopsidosis), systemic mycoses (e.g. chromomycosis, coccidiomycosis and histoplasmosis).

The pathogenic or facultatively pathogenic organisms from the yeast group include Candida species (e.g. *Candida albicans*) and those of the Pityrosporum family. Pityrosporum species, in particular *Pityrosporum ovale*, are responsible for skin diseases such as pityriasis versicolor, seborrhoea in the forms of seborrhoea oleosa and seborrhoea sicca, which are principally manifested as seborrhoea capitis (=dandruff), seborrhoeic eczema and *Pityrosporum folliculitis*.

All areas of the human skin can be affected by dermatomycoses. Dermatophytoses almost exclusively affect skin, hair and nails. Yeast mycoses can also affect mucous membranes and internal organs; systemic mycoses regularly extend to entire organ systems.

However, bacterial infections and superinfections of the skin can also, in particular in immunocompromised persons e.g. atopics and psoriatics, and also in diseases of another origin, cause considerable mental trauma. Superinfections denote the appearance in excessive numbers of organisms which are, per se, customarily found on the skin.

Those regions of the body are particularly frequently affected on which moisture and heat can accumulate due to the presence of clothing, jewellery or footwear. Thus, mycosis pedis is one of the best known and most widely disseminated dermatomycoses. In addition to this, fungal diseases of the finger nail and toe nail regions are particularly unpleasant.

Not all individuals of a population of microorganisms are viable. Organisms which form colonies on nutrient agar or suspensions in nutrient solutions are living, that is replicating, cells. A counting chamber or an electronic "Coulter counter" can be used to determine the total call count. In order to determine the viable cell count, the colonies which result from living cells can, for example, be counted. To do this, it is necessary to make use of dilute cell suspensions. The person skilled in the art is very familiar with such methods.

However, for clinical analysis and diagnosis, and these terms are intended equally to encompass dermatological analysis of the diseased human skin in the sense of a medical examination, and also cosmetic examination of skin which is healthy per se but which exhibits cosmetic, microbially engendered changes, no methods exist which, in the shortest possible time and while making the least possible demands on the patient, enable organism numbers to be detected qualitatively or to be counted quantitatively in a reliable manner. In this respect, it was necessary to take remedial action.

Over and above this, the conventional counting methods of the state of the art suffered from additional disadvantages, in particular either that of being unreliable or that of requiring an increased level of investment in apparatus, labour and/or time.

It was, therefore, the object of the present invention to remedy the defects of the state of the art. In particular, the intention was to make available methods for qualitatively detecting and/or quantitatively counting organism numbers, which methods provide reproducible results in a simple and rapid manner.

Furthermore, it was an object of the present invention to make available methods which are relatively easy to automate.

Another object of the present invention was to make available methods which ensure simple sampling without a sample still having to be worked up in an elaborate and time-consuming manner before carrying out the actual method.

Yet another object of the present invention was to make available methods which are, as far as possible, universally suitable for the greatest possible variety of organisms.

Finally, an object of the present invention was to make available methods which are especially suitable for counting microorganisms with regard to representatives of the flora of the human skin.

The achievement of all these objects is provided by a cosmetic or dermatological method for detecting and/or selectively quantifying individual microorganisms, and/or whole groups of microorganisms, which are present on human or animal skin, characterized in that after removing a sample of the microflora of the human or animal skin,

- this sample is treated with a deinhibiting medium, the sample which has been prepared in this way is added to a culture medium which exhibits favourable growth conditions for a defined group of microorganisms but unfavourable growth conditions for other microorganisms, as a result of which a selective culture is produced, and this selective culture is incubated over a sufficiently long period of time, such that only the group of microorganisms for which the culture medium exhibits favourable growth conditions has the opportunity to multiply, in association with which metabolic products, in particular $CO_2$, are produced which collect either in the culture medium itself or in a test vessel which is provided for the purpose and which contains an indicator medium, and
- the concentration of the metabolic products is elucidated by means of the change in the alternating current (AC) resistance of the culture medium and/or the indicator medium in the test vessel and, after appropriate calibration, is correlated by means of arithmetical methods with the number of microorganisms in the selective medium.

It is indeed known, per se, to undertake AC resistance measurements (impedance measurements) when analysing the metabolic processes of microorganisms. Thus, for example, P. Jakech ("Grundlagen der Impedanztechnik und Erfahrungen bei der Untersuchung roher und pasteurisierter Milch (Fundamental principles of the impedance technique and experiences in investigating raw and pasteurized milk)" in: dmZ Lebensmittelindustrie und Milchwirtschaft Vol. 31, 1991, pp. 950–960; "Nachweis von Hefen in Joghurt und Frischkase mittels indirekter Leitfahigkeitsmessung (Detection of yeasts in yoghurt and cream cheese by means of indirect conductivity measurement)" in: dmZ Lebensmittelindustrie und Milchwirtschaft Vol. 32/33, 1991, pp. 992–996) reports experiments on milk and milk products. However, it was not possible for the skilled person educated in dermatology or cosmetics to be guided by the methods disclosed in the cited references to the dermatological and/or cosmetic analytical methods which are presented here as being in accordance with the invention.

In particular, the skilled person would have had to assume that it was not possible to take representative and reproducible samples of the human or animal skin microflora, and to process them. The foodstuffs technician, for whom food product samples are available in quantities which are large and highly reproducible by comparison, is operating under conditions which are simply completely different from those of the dermatologist or cosmetician, who has to attempt to isolate representative quantities of a microorganism—which is, furthermore, still unknown to him—from the skin.

The use of alternating current is essential to the present invention, since the use of direct current would lead to electrolytic decomposition of the test medium and consequently to an uncontrollable change in the measured parameters.

The AC resistance of an object is made up of the following individual phenomena: the ohmic or nonreactive resistance, the inductive resistance and the capacitive resistance of the object. The reciprocal of the ohmic resistance is termed conductivity.

When carrying out measurements on liquid solutions, inductive effects are generally of no importance. The AC resistance Z, also termed impedance, is calculated from the parameters $G_O$=conductivity of the medium $G_B$=effect of the microbial metabolic activity on the conductivity of the medium $\Omega$=frequency of the alternating current C =capacitive resistance of the medium to be:

$$Z = \sqrt{1/(G_0 + G_B)^2 + 1/(\Omega C)^2}$$

The term $1/(G_O+G_B)$ describes the reciprocal of the ohmic resistance of the medium. The variable $G_B$ depends on the metabolic activity of the microorganism to be detected; $G_O$ is constant. The term $1/(\Omega C)$ relating to the capacitive resistance can be regarded as being constant during a measurement, so that, under the measurement conditions to be selected, the change in the impedance during a measurement only depends on $G_B$.

Due to the fact that the choice of a particular selective medium according to the invention ensures that, in each case, only one single microorganism species, or microorganism genus, whose metabolic activity brings about the change in impedance, is detected in each operational cycle, it is possible, by appropriate calibration, directly to assign a particular number of the microorganism to be detected, which number unambiguously relates to this microorganism, to a particular measured value for the impedance of the microorganism sample at any given time point.

Consequently, qualitative detection is achieved by the choice of the selective medium. Determination of the number of microorganisms of a particular species which are present in a sample correlates in turn with the concentration of the metabolic products, which concentration can, in accordance with the invention, be determined by measuring the impedance.

There are no important restrictions, per se, as regards the impedance measurement instruments which are to be used in accordance with the invention. It turned out, for example, that the instruments manufactured by Don Whitley Scientific Limited (Shipley, West Yorkshire, United Kingdom) and marketed under the name RABIT (=rapid automated bacterial impedance technique) meet the requirements very satisfactorily. In the Federal Republic of Germany, these instruments are sold by Mast Diagnostica. However, the instruments produced by other manufacturers, for example Malthus or Sylab, are also very well suited to the invention.

In principle, two methods have proved to be convenient for measuring the impedance of the microorganism sample.

BRIEFED DESCRIPTION OF DRAWINGS

The first of these is the direct measurement method which is depicted in FIG. 1 and in which two electrodes (A, A') are inserted directly in the selective medium (B) and the change in the impedance is monitored over the measurement period. FIG. 1 shows, in diagrammatic form, the wiring diagram for a resistance measurement, with the measurement instrument designated by V representing a voltmeter and the instrument designated by A representing an ammeter. The overall resistance Z is calculated in accordance with Ohm's law, $Z=U/I$ (voltage/current).

Figure 2:
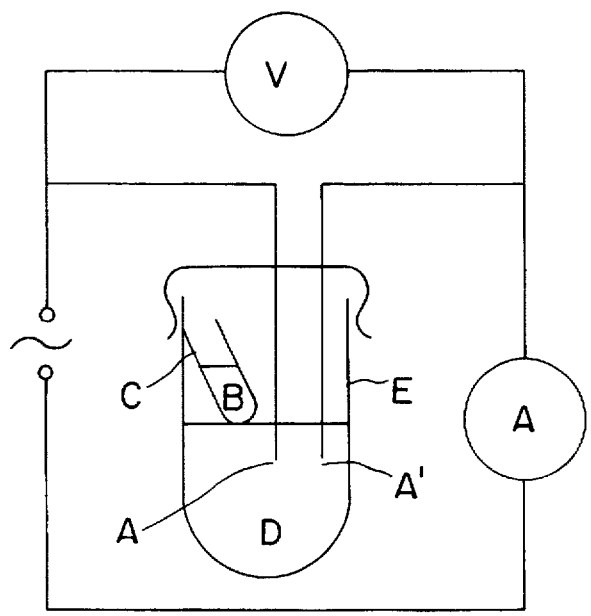

The second measurement method, which is depicted in FIG. 2, is preferred, in particular, in the case of microorganisms which produce large quantities of $CO_2$. In this case, the microorganism sample is present in selective medium (B) in a vessel (C). This vessel is connected, by way of the air space, with an indicator medium (D) which captures the gaseous metabolic products which are produced by the microorganism sample or the microorganism colony which is being formed in the sample. Both the vessel (C) and the indicator medium (D) are located in a vessel (E) which is sealed in a gas-tight manner. The measurement electrodes (A, A') are inserted into this indicator medium. That which was said in relation to FIG. 1 applies as regards calculating the resistance Z. KOH-agar has been found to be a particularly advantageous indicator medium.

The following method of measurement has been found to be particularly suitable: A signal is emitted by the measuring station at a defined threshold value for the alteration of the impedance of the sample, which value normally corresponds to a microorganism concentration of $10^5$/ml and corresponds to approximately $-10$ μS (microsiemens) in the case of the indirect method and approximately 5 μS in the case of the direct method. The preceding negative sign is due to the fact that the conductivity of the indicator medium (KOH-agar) decreases as a result of the absorption of the $CO_2$ which is produced.

If the microorganism cultures are of different individual concentrations, all of which lie below the limit concentration, and are subjected to (where appropriate selective) growth conditions, the time within which the limit concentration is reached in the individual samples, and the signal is emitted, is proportional to the logarithm of the initial individual concentration.

Consequently, if the experimental structure is calibrated with cultures of known microorganisms having known individual concentrations, a sample of unknown microorganisms of unknown individual concentration can then be examined for the nature of the microorganism by means of the choice of selective medium, and be analysed for its concentration by means of detection in the impedance measurement instrument using the previously described measurement method.

The commercially available instruments for measuring impedance customarily operate in accordance with this method.

It has been found to be advantageous, in particular when the object from which the microorganism sample is to be taken is the human skin, to choose methods of sampling as described by A. A. Hartmann in "Untersuchungen zu Unterschieden der Keimzahlen der Residentflora benachbarter Hautareale in Abhängigkeit von der benutzten Hautfloragewinnungsmethode (Investigations of the influence of the method of skin flora isolation employed on differences in the organism numbers of the resident flora of adjacent areas of the skin)", Ärztliche Kosmetologie Vol. 13, pp. 142–154 (1983) (published by Verlag G. Braun, Karlsruhe).

In the abovementioned article, whose content is an advantageous constituent of the teaching disclosed herewith, and to which reference is made for the sake of simplicity, the following main methods for isolating skin flora are described and/or cited:
1.) The detergent washing method ("DWM")
2.) The cyanoacrylate method ("CyAM")
3.) The water-pick method ("S & N")
4.) The water spray method ("Thran")

It is particularly advantageous to use the detergent washing method, in particular in the modification described below:

A skin area of defined size is rinsed for a defined period of time with a defined quantity of an aqueous solution of a surface-active agent, with this aqueous solution advantageously being buffered to a pH between 5.0 and 8.0, and with the said skin area advantageously being simultaneously scraped, while exerting gentle pressure, with a scraping tool, in particular a spatula which is coated with a synthetic material (for example Teflon).

Although, in principle, all surface-active agents which are cosmetically or dermatologically suitable can be used in accordance with the invention, it can, nevertheless, be advantageous, where appropriate, to use those agents which, if anything, inhibit the growth of certain microorganisms and have no effect, or only slight effect, on the growth of other microorganisms. The same applies to the choice of the pH and/or to the buffering agent itself: in principle, all buffers which are cosmetically of dermatologically suitable can be used in accordance with the invention, although it can be advantageous, where appropriate, also to exert, by means of the choice of the buffer, a certain selection pressure on the microorganism sample.

The sample which has thus been obtained is then treated with a deinhibiting medium. It can then be combined with a selective medium, as nutrient base, with it being perfectly possible to allow a period of up to six hours to elapse between these two latter events.

A deinhibiting medium is understood to be a medium which effects a repair of the bacteria which have been damaged by the rinsing.

Deinhibiting media which are preferred in accordance with the invention are distinguished by the following compositions:

| Brain/heart extract and peptone | 0 to 50 g/l |
|---|---|
| D-(*)-glucose | 0 to 5 g/l |
| NaCl | 0 to 20 g/l |
| $Na_2HPO_4 * H_2O$ | 0 to 10 g/l |
| Tween 80 | 0 to 50 g/l |
| Lecithin | 0 to 5 g/l |
| Histidine | 0 to 5 g/l |

The substance mixture is advantageously dissolved in 1.0 liter of distilled water, the solution autoclaved and the pH adjusted to 5.5 to 8.5.

The detection method is based on the fact that the detected metabolic product, preferably $CO_2$, alters the resistance of the test medium or indicator medium.

Culture media which exhibit favourable growth conditions for certain groups of microorganisms but unfavourable growth conditions for other groups of microorganisms are also regarded as a particularly advantageous embodiment of the present invention. In connection with the present invention, such media are designated selective media.

Selective media which are preferred in accordance with the invention are described more precisely below. Nevertheless, other selective media, which belong, per se, to the state of the art, can also be used within the scope of the novel methods.

In an individual case, it is possible that a certain selective medium can be used as a selective medium for several organisms which differ per se. However, this is not an inconsistency since additional mechanisms are available for restoring the unambiguousness of the selective medium, e.g. streptococci will predominantly be found in the oral cavity and use can, nevertheless, be made of a selective medium which reacts to streptococci and Enterococci.

Although the novel selective media can extremely advantageously be used as compositions for the novel dermatological or cosmetic detection methods, their spectrum of use is not restricted to these methods.

Thus, these selective media can, for example, be used in other detection methods or else in methods for culturing microorganisms.

The novel selective media are characterized by a base medium, which serves as nutrient source for microorganisms, and, in addition to this, by one or more substances which, while inhibiting the growth of certain microorganisms, leave other microorganisms, namely those which are to be detected, unaffected.

Staphylococci:

Novel selective media for Staphylococci consist of 40–50 parts by weight of a customary base medium to which are added a single substance or a substance mixture (termed selector or selectors, respectively, within the scope of the present patent application), chosen from the following constituents:

|  | Parts by weight |
| --- | --- |
| Sodium pyruvate | 0.2 to 20.0 |
| Glycine | 0.05 to 5.0 |
| KSCN | 0.05 to 5.0 |
| $NaH_2PO_4$ | 0.05 to 2.0 |
| $Na_2HPO_4$ | 0.02 to 2.0 |
| LiCl | 0.1 to 10.0 |
| Aztreonam | 0 to 0.01 |
| Linolenic acid | 0 to 50.0 |

Advantageously, the lower limit of selectors is 2 parts by weight to 50 parts by weight of base medium.

Astonishingly, it is possible to differentiate between Staphylococci, in particular between *Staphylococcus aureus* and *Staphylococcus epidermidis*, by means of adding linolenic acid. *Staph. epidermidis* is capable of growth in the presence of linolenic acid, in contrast to *Staph. aureus*, whose growth is inhibited.

A base medium which is favourable for preparing a selective medium for Staphylococci has the following composition, for example:

|  | Parts by weight |
| --- | --- |
| Casein peptone | 10.0 |
| Meat extract | 5.0 |
| Yeast extract | 3.0 |
| Glycerol | 10.0 |
| Agar | 13.0 |

However, the person skilled in the art is very familiar with the composition of a base medium which promotes the growth of microorganisms, so that this matter will not be gone into in any further detail at this point. This also applies to the other base media which are disclosed in this description.

Propionibacterium spec.:

Novel selective media for Propionibacterium spec. consist of 35–50 parts by weight of a customary base medium to which one or more selectors are added which are chosen from the following constituents:

|  | Parts by weight |
| --- | --- |
| Sodium thioglycolate | 0.05 to 5.0 |
| NaCl | 0.1 to 10.0 |
| L-Cysteine HCl | 0.05 to 5.0 |
| Resazurin | 0.001 to 0.10 |
| $NaHCO_3$ | 0.05 to 5.0 |
| Phosphomycin | 0.01 to 1.0 |

Advantageously, the lower limit of selectors is 0.5 parts by weight to 50 parts by weight of base medium.

A base medium which is favourable for preparing a selective medium for Propionibacterium spec. has the following composition, for example:

|  | Parts by weight |
| --- | --- |
| Peptone | 15.0 |
| Yeast extract | 10.0 |
| Agar | 15.0 |

Anaerobic organisms:

Novel selective media for anaerobic organisms consist of 35–50 parts by weight of a customary base medium to which one or more selectors are added which are chosen from the following constituents:

|  | Parts by weight |
| --- | --- |
| Sodium thioglycolate | 0.05 to 5.0 |
| NaCl | 0.1 to 10.0 |
| L-Cysteine HCl | 0.05 to 5.0 |
| Resazurin | 0.001 to 0.10 |
| $NaHCO_3$ | 0.05 to 5.0 |

Advantageously, the lower limit of selectors is 0.5 parts by weight to 50 parts by weight of base medium.

A base medium which is favourable for preparing a selective medium for anaerobic organisms has the following composition, for example:

|  | Parts by weight |
| --- | --- |
| Peptone | 15.0 |
| Yeast extract | 10.0 |
| Agar | 15.0 |

Pityrosporum spec.:

Novel selective media for Pityrosporum spec. consist of 40–90 parts by weight of a customary base medium to which one or more selectors are added which are chosen from the following constituents:

|  | Parts by weight |
| --- | --- |
| Glycerol monostearate | 0.05 to 5.0 |
| Tween 80 | 0.05 to 5.0 |
| Chloramphenicol | 0.01 to 1.0 |
| Gentamycin | 0.005 to 0.5 |

Advantageously, the lower limit of selectors is 0.1 parts by weight to 50 parts by weight of base medium.

A base medium which is favourable for preparing a selective medium for Pityrosporum spec. has the following composition, for example:

|  | Parts by weight |
| --- | --- |
| Neopeptones | 15.0 |
| Yeast extract | 0.1 |
| Agar | 18.0 |
| Olive oil | 20.0 |

Yeasts, for example of the genus Candida:

Novel selective media for yeasts, for example of the genus Candida, consist of 30–50 parts by weight of a customary base medium to which one or more selectors are added which are chosen from the following constituents:

|  | Parts by weight |
| --- | --- |
| Bismuth sulphite | 0.1 to 10.0 |
| Neomycin | 0.005 to 0.5 |

Advantageously, the lower limit of selectors is 0.05 parts by weight to 50 parts by weight of base medium.

A base medium which is favourable for preparing a selective medium for yeasts has the following composition, for example:

|  | Parts by weight |
| --- | --- |
| Yeast extract | 1.0 |
| Agar | 15.0 |
| Glycocoll | 10.0 |
| Glucose | 10.0 |

Moulds and dermatophytes:

Novel selective media for moulds and dermatophytes consist of 20–75 parts by weight of a customary base medium to which from 10 to 100 parts by weight of NaCl are added.

Enterococci and streptococci:

Novel selective media for Enterococci, and also for streptococci (for example *Streptococcus mutans*), consist of 30–60 parts by weight of a customary base medium to which one or more selectors are added which are chosen from the following constituents:

|  | Parts by weight |
| --- | --- |
| Sodium citrate | 0.5 to 50.0 |
| Sodium azide | 0.1 to 10.0 |
| Thallium acetate | 0.2 to 20.0 |
| 2,3,5-Triphenyltetrazole (or its acid adducts) | 0.001 to 0.10 |

Advantageously, the lower limit of selectors is 5 parts by weight to 50 parts by weight of base medium.

A base medium which is favourable for preparing a selective medium for enterococci, and also streptococci (for example *Streptococcus mutans*), has the following composition, for example:

|  | Parts by weight |
| --- | --- |
| Casein peptone | 10.0 |
| Agar | 15.0 |
| Meat extract | 10.0 |
| Glucose | 10.0 |

Coryneform organisms and Corynebacterium:

Novel selective media for coryneform organisms and also Corynebacterium consist of 30–50 parts by weight of a customary base medium to which one or more selectors are added which are chosen from the following constituents:

|  | Parts by weight |
| --- | --- |
| Furazolidone (Aldrich) | 0.5 to 50.0 |
| Acetone | 0.5 to 50.0 |
| Tween 80 | 0.1 to 10.0 |
| Bovine serum | 2.0 to 200 |
| Phosphomycin (Sigma Chemicals) | 5.0 to 500 |
| Autoclaved water | ad 1000 |

A base medium which is favourable for preparing a selective medium for coliform organisms and also *E. coli* has the following composition, for example:

|  | Parts by weight |
| --- | --- |
| Caso-agar | 44.00 g |
| Yeast extract | 1.10 g |
| Deionized water | ad 1000.00 ml |

Coliform organisms and *E. coli*:

Novel selective media for coliform organisms and also *E. coli* consist of 30–50 parts by weight of a customary base medium to which one or more selectors are added which are chosen from the following constituents:

|  | Parts by weight |
| --- | --- |
| NaCl | 0.1 to 10.0 |
| Lactose | 0.2 to 20.0 |
| Basic fuchsin | 0.02 to 2.0 |
| $Na_2SO_3$ | 0.05 to 5.0 |

Advantageously, the lower limit of selectors is 2 parts by weight to 40 parts by weight of base medium.

A base medium which is favourable for preparing a selective medium for coliform organisms and also *E. coli* has the following composition, for example:

|  | Parts by weight |
| --- | --- |
| Peptone from meat | 10.0 |
| Agar | 20.0 |
| Meat extract | 10.0 |

Enterobacteriaceae:

Novel selective media for Enterobacteriaceae, which completely suppress the growth of Gram-positive bacteria and coliform organisms, consist of 30–55 parts by weight of a customary base medium to which one or more selectors are added which are chosen from the following constituents:

|  | Parts by weight |
| --- | --- |
| Sodium citrate | 0.1 to 10.0 |
| $Na_2S_2O_3$ | 0.1 to 10.0 |
| Sodium deoxycholate | 0.1 to 10.0 |
| Ammonium iron (III) citrate | 0.05 to 5.0 |
| Neutral red | 0.001 to 0.1 |

Advantageously, the lower limit of selectors is 5 parts by weight to 40 parts by weight of base medium.

A base medium which is favourable for preparing a selective medium for Enterobacteria has the following composition, for example:

|  | Parts by weight |
| --- | --- |
| Peptone | 5.0 |
| Agar | 13.0 |
| Meat extract | 5.0 |
| Lactose | 10.0 |
| Sucrose | 10.0 |

According to the invention, it is particularly advantageous to use the method as a cosmetic or dermatological detection method. In this context, the facts to be investigated are changes in the microflora of the skin. Naturally, the boundaries between a cosmetic and a dermatological investigation are fluid.

In the first instance, the main focus of cosmetic detection in accordance with the invention lies in determining the change in the absolute or relative numbers of organisms, and less in detecting specific organisms. Nevertheless, detection of the presence of particular apathogenic organisms is also an advantageous embodiment of the novel methods in the case of certain cosmetic skin changes, for example in the case of body odour (head, foot and axillary odour) and dirty skin, and in oral hygiene and all other cosmetic skin changes in which microorganisms are involved.

Dermatological detection according to the invention essentially consists in determining pathological changes in the microflora of the skin. In this case too, both the presence and also the number of organisms concerned can advantageously be determined in accordance with the invention. Examples of advantageous novel methods are those for detecting the following dermatological manifestations:
atopic eczema
psoriasis
acne
seborrhoeic dematitis
cellulitis caused by bacteria
dermatomycoses
superinfections of the skin with pathogenic and/or apathogenic Gram-positive and/or Gram-negative microorganisms The following examples demonstrate advantageous embodiments of the selective media which are to be used in accordance with the invention.

EXAMPLE 1

A particularly advantageous selective medium for Staphylococci is distinguished by the following composition:

| Casein peptone | 10.00 g |
| --- | --- |
| Meat extract | 5.00 g |
| Yeast extract | 3.00 g |
| Glycerol | 10.00 g |
| Na pyruvate | 10.00 g |
| Glycine | 0.50 g |
| KSCN | 2.25 g |
| $NaH_2PO_4*H_2O$ | 0.60 g |
| $Na_2HPO_4*2H_2O$ | 0.90 g |
| LiCl | 2.00 g |
| Agar | 13.00 g |

The components are dissolved in 1 l of water, and the solution is autoclaved and the pH is adjusted to 7.2. After the solution has been cooled down to approximately 50° C., 10 ml of a 0.45% solution of sodium azide are added and the mixture is poured into small agar slope tubes.

The medium selects for staphylococci. Coryneform bacteria do not exhibit any growth, and Micrococcus spec. only grows to a noticeable extent after about 40 hours, that is well outside the detection time for Staphylococci.

EXAMPLE 1a

Another, particularly advantageous, selective medium for Staphylococci is distinguished by the following composition:

| Casein peptone | 8.50 g |
| --- | --- |
| Liver peptone | 2.00 g |
| Yeast extract | 2.00 g |
| Lactalbumin | 5.50 g |
| Na pyruvate | 10.00 g |
| Glycine | 0.50 g |
| $NaH_2PO_4*H_2O$ | 0.60 g |
| $Na_2HPO_4*2H_2O$ | 0.90 g |
| LiCl | 5.00 g |
| Aztreonam | 0.005 g |
| Agar | 13.00 g |

The components are dissolved in 1 l of water, and the solution is autoclaved and the pH is adjusted to 7.2. After the solution has been cooled down to about 50° C., the mixture is poured into small agar slope tubes.

The medium selects for Staphylococci.

EXAMPLE 1b

An advantageous selective medium for *Staphylococcus epidermidis* as compared with *Staphylococcus aureus* is distinguished by the following composition:

| Casein peptone | 8.50 g |
| --- | --- |
| Liver peptone | 2.00 g |
| Yeast extract | 2.00 g |
| Lactalbumin | 5.50 g |
| Na pyruvate | 10.00 g |
| Glycine | 0.50 g |
| $NaH_2PO_4*H_2O$ | 0.60 g |
| $Na_2HPO_4*2H_2O$ | 0.90 g |
| LiCl | 5.00 g |
| Aztreonam | 0.005 g |
| Linolenic acid | 0.60 g |
| Agar | 13.00 g |

The components are dissolved in 1 l of water, and the solution is autoclaved and the pH is adjusted to 7.2. After having been cooled down to about 50° C., the mixture is poured into small agar slope tubes.

In this medium, *Staphylococcus aureus* cannot be detected even after a detection time of 40 hours.

EXAMPLE 2

A particularly advantageous selective medium for Propionibacterium spec. is distinguished by the following composition:

| | |
|---|---|
| Peptone | 15.0 g |
| Yeast extract | 10.0 g |
| Sodium thioglycolate | 0.5 g |
| NaCl | 2.5 g |
| L-Cysteine HCl | 0.5 g |
| Resazurin | 0.001 g |
| $NaHCO_3$ | 0.4 g |

The substance mixture is dissolved in 1.0 l of distilled water and the solution is autoclaved. After it has been cooled down to 50° C., 160 mg of phosphomycin are added per liter of medium and the pH is adjusted to 7.2.

EXAMPLE 3

A particularly advantageous selective medium for anaerobic organisms is distinguished by the following composition:

| | |
|---|---|
| Peptone | 15.0 g |
| Yeast extract | 10.0 g |
| Sodium thioglycolate | 0.5 g |
| NaCl | 2.5 g |
| L-Cysteine HCl | 0.5 g |
| Resazurin | 0.001 g |
| $NaHCO_3$ | 0.4 g |

The substance mixture is dissolved in 1.0 l of distilled water and the solution is autoclaved. The pH is adjusted to 7.2. The actual detection method is carried out under anaerobic conditions.

EXAMPLE 4

A particularly advantageous selective medium for Pityrosporum spec. is distinguished by the following composition:

| | |
|---|---|
| Neopeptones | 15.0 g |
| Yeast extract | 0.1 g |
| Agar | 18.0 g |
| Olive oil | 20.0 g |
| Glycerol monostearate | 2.5 g |
| Tween 80 | 2.0 g |

The substance mixture is made up to 1.0 liter with distilled water and the pH is adjusted to 6.0. The medium is then autoclaved. The medium, which is still liquid, is allowed to cool to approximately 50° C., and 100 mg of chloramphenicol and 50 mg of gentamycin are added per liter. The medium is then poured into small agar slope tubes.

EXAMPLE 5

A particularly advantageous selective medium for yeasts, in particular those of the genus Candida, is distinguished by the following composition:

| | |
|---|---|
| Yeast extract | 2.0 g |
| Agar | 15.0 g |
| Glycocoll | 10.0 g |

| | |
|---|---|
| Glucose | 10.0 g |
| Bismuth sulphite | 7.0 g |

The substance mixture is dissolved in 1.0 liter of distilled water and the solution is heated to boiling. After cooling down to approximately 50° C., 2.0 mg of neomycin sulphate are added/l and the medium is then poured into small agar slope tubes.

EXAMPLE 6

A particularly advantageous selective medium for enterococci and also streptococci (for example *Streptococcus mutans*) is distinguished by the following composition:

| | |
|---|---|
| Casein peptone | 10.0 g |
| Agar | 15.0 g |
| Meat extract | 10.0 g |
| Glucose | 10.0 g |

The above substance mixture for the base medium is dissolved in 1.0 l of distilled water and the solution is autoclaved. After it has been cooled down, the following are added: 20.0 g of sodium citrate, 0.02 g of sodium azide, 30 ml of a sterile, aqueous 5% solution of thallium(III) acetate, and 10.0 ml of a sterile, aqueous 1% solution of 2,3,5-triphenyltetrazolium chloride. The pH of the resulting selective medium is adjusted to 6.2 and the medium is poured into small agar slope tubes.

The medium is particularly well suited for detecting faecal organisms. Streptococci which lead to the development of caries can equally well be detected, as can antimicrobial active principles which are directed against these organisms (in particular *Streptococcus mutans*) and which can be contained in compositions for treating teeth.

EXAMPLE 7

A particularly advantageous selective medium for coryneform organisms and also corynebacteria is distinguished by the following composition:

| Mixture A | |
|---|---|
| Caso-agar | 44.00 g |
| Yeast extract | 1.10 g |
| Water | ad 1000.00 ml |

The mixture is autoclaved and allowed to cool to 50° C.

| Mixture B | |
|---|---|
| Furazolidone (Aldrich) | 22.00 mg |
| Acetone | 22.00 ml |
| Tween 80 | 5.50 ml |
| Bovine serum | 100.00 ml |
| Phosphomycin (Sigma Chemicals) | 168.00 ml |
| Autoclaved water | 16.80 ml |

The furazolidone is dissolved in the 22 ml of acetone, and the phosphomycin is dissolved in the 16.8 ml of autoclaved water. The components of mixture B are then added to each other and the resulting mixture is combined with mixture A.

EXAMPLE 8

A particularly advantageous selective medium for coliform organisms and also *E. coli* is distinguished by the following composition:

| | |
|---|---|
| Peptone from meat | 10.0 g |
| Agar | 20.0 g |
| Meat extract | 10.0 g |
| NaCl | 5.0 g |
| Lactose | 10.0 g |
| Basic fuchsin | 0.5 g |
| $Na_2SO_3$ | 2.5 g |

The above substance mixture for the base medium is dissolved in 1.0 l of distilled water and the solution is autoclaved. If the medium has a reddish colour after autoclaving, a little additional sodium sulphite is added until the reddish hue has disappeared. The medium is then poured into small agar slope tubes.

The selective medium must be used immediately after it has solidified. After only a few days, it stains a reddish colour, which indicates that it has become unusable.

EXAMPLE 9

A particularly advantageous selective medium for Enterobacteriaceae is distinguished by the following composition:

| | |
|---|---|
| Peptone | 5.0 g |
| Agar | 13.0 g |
| Meat extract | 5.0 g |
| Lactose | 10.0 g |
| Sucrose | 10.0 g |
| Sodium citrate | 6.0 g |
| $Na_2S_2O_3$ | 4.0 g |
| Sodium deoxycholate | 3.0 g |
| Ammonium iron (III) citrate | 1.0 g |
| Neutral red | 0.02 g |

The above substance mixture is dissolved in 1.0 l of distilled water and the solution is heated to boiling. After the agar has been dissolved, the mixture is poured into small agar slope tubes and allowed to solidify.

The medium can also be used in clinical diagnosis, for example for detecting salmonellas, shigellas, vibrios and pathogenic yersinias.

EXAMPLE 10

A particularly advantageous selective medium for moulds is distinguished by the following composition:

| | |
|---|---|
| Malt extract | 20.0 g |
| NaCl | 75.0 g |
| Agar | 15.0 g |

The substance mixture is dissolved in 1.0 liter of distilled water and the solution is autoclaved and poured into small agar slope tubes.

The medium is also suitable for culturing dermatophytes and for detecting the antimycotic properties of test substances towards these organisms.

EXAMPLE 11

Deinhibiting medium

| | |
|---|---|
| Brain/heart extract and peptone | 27.5 g |
| D-(*)-glucose | 2.0 g |
| NaCl | 5.0 g |
| $Na_2HPO_4*H_2O$ | 2.5 g |
| Tween 80 | 30.0 g |
| Lecithin | 3.0 g |
| Histidin | 1.0 g |

The substance mixture is dissolved in 1.0 liter of distilled water, and the solution is autoclaved and the pH is adjusted to 7.4.

Experiment I:

(1) Calibration of the impedance system for Staphylococci using a reference strain and using wild-type isolates

*Staphylococcus epidermidis* DSM 20044 was used as the reference strain. A calibration series consisting of thirty four different numbers of organisms was prepared by dilution and the impedance system was calibrated using this calibration series.

The lowest organism concentration (CFU) was $3.3 * 10^1$/ml, corresponding to a time of 22 hours and 24 minutes for reaching the threshold value of $-10$ µS; the highest concentration was $1.3 * 10^7$/ml, corresponding to a time of 3 hours and 12 minutes for reaching the threshold value of $-10$ µS.

A straight-line calibration was obtained having the relationship $$\log (CFU/ml) = mT+c$$

where $$m = -0.255 \text{ Log (CFU/ml)/hr}$$

$$c = 7.070 \log (CFU/ml).$$

The correlation coefficient of the linear regression was $-0.942$.

A mixture of staphylococci which had been isolated from the armpit region was used as wild-type isolates. A dilution series consisting of fifty one different numbers of organisms was prepared and used for calibrating the impedance system.

A straight-line calibration was obtained having the relationship $$\log (CFU/ml) = mT+c$$

where $$m = -0.204 \log (CFU/ml)/hr$$

$$c = 7.860 \log (CFU/ml).$$

The correlation coefficient of the linear regression was $-0.917$.

(2) Method for isolating microorganisms from the skin and for detecting and quantifying skin staphylococci by means of indirect impedance measurement The entire microflora of a region of the human skin (e.g. of the axilla) is isolated by rinsing an area of 3.8 $cm^2$ over a period of one minute with 1 ml of 0.075 molar phosphate buffer (pH=7.9), containing 0.1% Triton X-100 as surface-active agent, while gently scraping with a Teflon-coated metal spatula.

The resulting sample is treated with 500 µl of deinhibiting medium in accordance with Example 11.

Each 100 µl of the sample which has been prepared in this way are treated with 2.4 ml of selective medium in accordance with Example 1, and the number of organisms is determined in the measurement device using the indirect detection method.

By means of this procedure, it was possible, without difficulty, to detect between $10^2$ and $10^7$ staphylococci per $cm^2$ of skin in the case of ten different test subjects.

A RABIT from Don Whitley Scientific Ltd. was used as the detection instrument.

Experiment II:

(1) Calibration of the impedance system for coryneform bacteria using a reference strain Corynebacterium spec. was used as the wild-type strain. A calibration series consisting of fifty one different numbers of organisms was prepared by dilution, and the impedance system was calibrated using this calibration series.

The lowest organism concentration (CFU) was $2.1 * 10^2$/ml, corresponding to a time of 51 hours and 48 minutes for reaching the threshold value of $-10$ µS; the highest concentration was $9.8 * 10^6$/ml, corresponding to a time of 10 hours and 24 minutes for reaching the threshold value of $-10$ µS.

A straight-line calibration was obtained having the relationship $$\log (CFU/ml) = mT + c$$

where $$m = -0.085 \log (CFU/ml)/hr$$

$$c = 7.380 \log (CFU/ml).$$

The correlation coefficient of the linear regression was $-0.883$.

(2) Method for isolating microorganisms from the skin and for detecting and quantifying coryneform bacteria by means of indirect impedance measurement The entire microflora of a region of the human skin (e.g. of the axilla) is isolated by rinsing an area of 3.8 $cm^2$ over a period of one minute with 1 ml of 0.075 molar phosphate buffer (pH=7.9), containing 0.1% Triton X-100 as surface-active agent, while gently scraping with a Teflon-coated metal spatula.

The resulting sample is treated with 500 µl of deinhibiting medium in accordance with Example 11.

Each 100 µl of the sample which has been prepared in this way are treated with 2.4 ml of selective medium in accordance with Example 7, and the number of organisms is determined in the measurement device using the indirect detection method.

By means of this procedure, it was possible, without difficulty, to detect between $10^2$ and $10^7$ coryneform bacteria or corynebacteria per $cm^2$ of skin in the case of ten different test subjects.

A RABIT from Don Whitley Scientific Ltd. was used as the detection instrument.

We claim:

1. A cosmetic or dermatological method for detecting or selectively quantifying nonpathological individual microorganism or whole groups of microorganisms or a pathological microorganism or whole groups of microorganisms which cause cosmetic disorders or dermatological diseases wherein said microorganisms are present on human or animal skin, said method comprises scraping a defined area on said skin to remove a sample of microflora;

treating the sample with a deinhibiting medium;

adding the sample obtained above into a culture medium which exhibits favorable growth conditions for the microorganisms or group of microorganisms but unfavorable growth for other microorganisms present in the microflora so that a selective culture is produced;

incubating the resulting selective culture for a time sufficient for the microorganisms to multiply and to produce metabolic products;

collecting the metabolic products either by collecting the culture medium itself or by collecting the products in a test vessel containing an indicator medium; and measuring, after calibration the concentration of metabolic products by measuring the change in the alternating current in the culture medium or the indicator medium and determining the number of microorganisms in the selective medium by arithmetic method.

2. The method according to claim 1, wherein the metabolic product is $CO_2$.

3. The method according to claim 1, wherein the skin is first rinsed for a defined period of time with an aqueous solution of a surface-active agent which is buffered to a pH between 5.0 to 8.0 and then scraped with a spatula.

4. The method according to claim 3, wherein the spatula is coated with a synthetic material.

5. The method according to claim 4, wherein the synthetic material is Teflon.

6. The method according to claim 1, wherein the selective medium is for testing Staphylococci and consists of 40 to 50 parts by weight of a customary base medium and one or more selectors selected from the group consisting of sodium pyruvate, glycin, KSCN, $NaH_2PO_4$, $Na_2HPO_8$, LiCl, aztreonam and linolenic acid.

7. The method according to claim 1, wherein the selective medium is for testing Propioni bacterium spec. and consists of 35 to 50 parts by weight of a customary base medium and one or more selectors selected from the group consisting of sodium thioglycolate, NaCl, L-cysteine, HCl, resazurin and $NaHCO_3$ and phosphomycin.

8. The method according to claim 1, wherein the selective medium is for testing anaerobic microorganisms and consists of 35 to 50 parts by weight of a customary base medium and one or more selectors selected from the group consisting of sodium thioglycolate, NaCl, L-cysteine, HCl, resazurin and $NaHCO_3$.

9. The method according to claim 1, wherein the selective medium is for testing Pityrosporum spec. and consists of 40 to 90 parts by weight of a customary base medium and one or more selectors selected from the group consisting of glycerol monostearate, Tween 80, chloramphenicol and gentamycin.

10. The method according to claim 1, wherein the selective medium is for testing yeasts and consists of 30 to 50 parts by weight of a customary base medium and one or more selectors selected from the group consisting of bismuth sulphite and neomycin.

11. The method according to claim 1, wherein the yeast is from the genus Candida.

12. The method according to claim 1, wherein the selective medium is for testing molds or for dermatophytes and consists of 20 to 75 parts by weight of a customary medium and NaCl as the selector.

13. The method according to claim 1, wherein the selective medium is for testing enterococci and consists of 30 to 60 parts by weight of a customary base medium and one or more selectors selected from the group consisting of sodium citrate, sodium azide, thallium acetate and 2,3,5-triphenyltetrazole.

14. The method according to claim 1, wherein the selective medium is for testing coliform organisms and consists of 30 to 60 parts by weight of a customary base medium and one or more selectors selected from the group consisting of NaCl, lactose, basic fuchsin and $Na_2SO_3$.

15. The method according to claim 14, wherein the coliform organism is *Escherchia coli*.

16. The method according to claim 1, wherein the selective medium is for testing Enterobacterieaceae and consists of 30 to 60 parts by weight of a customary base medium and one or more selectors selected from the group consisting of sodium citrate, $Na_2S_2O_3$, sodium deoxycholate, ammonium icon (III) citrate and neutral red.

17. The method according to claim 1, wherein the dermatological disease is atopic eczema psoriasis acne seborrheoic dermatitis cellulitis caused by bacteria dermatomycoses superinfections of the skin with pathogenic and/or apathogenic Gram-positive and/or Gram-negative microorganisms.

* * * * *